United States Patent [19]

Puglia et al.

[11] 4,271,142

[45] Jun. 2, 1981

[54] PORTABLE LIQUID ANTACIDS

[75] Inventors: Wayne J. Puglia, Bellerose Village; Frank Witzel, Spring Valley; Donald A. M. Mackay, Pleasantville, all of N.Y.

[73] Assignee: Life Savers, Inc., New York, N.Y.

[21] Appl. No.: 170,469

[22] Filed: Jul. 21, 1980

Related U.S. Application Data

[63] Continuation-in-part of Ser. No. 49,535, Jun. 18, 1979, abandoned.

[51] Int. Cl.³ .......................... A61K 9/24; A61K 9/28; A61K 9/42; A61K 33/06
[52] U.S. Cl. .................................... 424/14; 424/16; 424/21; 424/38; 424/154; 424/155; 424/156; 424/157; 424/158; 426/89; 426/103; 426/138; 426/306; 426/534; 426/548; 426/593; 426/607; 426/658; 426/660
[58] Field of Search ................. 424/14, 16, 21, 38, 424/154–158; 426/89, 103, 138, 306, 534, 548, 593, 607, 658, 660

[56] References Cited

U.S. PATENT DOCUMENTS

| | | | |
|---|---|---|---|
| 780,226 | 1/1905 | Pink | 424/38 |
| 1,546,820 | 7/1925 | Ballard et al. | 424/38 |
| 1,851,165 | 3/1932 | Farr | 424/38 |
| 1,991,139 | 2/1935 | Clark | 424/38 |
| 2,461,399 | 2/1949 | Strausser | 426/103 |
| 2,477,080 | 7/1949 | Necheles et al. | 424/156 |
| 2,682,471 | 6/1954 | Alther | 426/103 |
| 2,836,540 | 5/1958 | Hardt | 424/157 |
| 2,843,521 | 7/1958 | Entrekin | 424/157 |
| 2,926,121 | 2/1960 | Hobbs et al. | 424/158 |
| 2,955,548 | 10/1960 | Himmler | 426/282 |
| 3,164,519 | 1/1965 | Puetzer et al. | 424/156 |
| 3,175,942 | 3/1965 | Anderson et al. | 424/157 |
| 3,215,601 | 11/1965 | Stolor | 424/157 |
| 3,253,988 | 5/1966 | Scott | 424/156 |
| 3,456,050 | 7/1969 | Rieckmann et al. | 424/38 |
| 3,536,074 | 10/1970 | Aufhauser | 424/14 |
| 3,577,533 | 5/1971 | Rider | 424/155 |
| 3,579,634 | 5/1971 | Brown | 424/154 |
| 3,591,680 | 7/1971 | Greene et al. | 424/156 |
| 3,692,898 | 9/1972 | Gorman et al. | 424/158 |
| 3,697,641 | 10/1972 | Ahrens | 424/38 |
| 3,843,778 | 10/1974 | Diamond et al. | 424/38 |

FOREIGN PATENT DOCUMENTS

| | | | |
|---|---|---|---|
| 187876 | 4/1905 | Fed. Rep. of Germany | 424/38 |
| 832932 | 3/1952 | Fed. Rep. of Germany | 424/38 |
| 1888/8869 | of 1889 | United Kingdom | 424/15 |
| 26/8941907 | of 1908 | United Kingdom | 424/156 |
| 392/1913 | of 1913 | United Kingdom | 424/156 |
| 471116 | 8/1937 | United Kingdom | 424/38 |
| 543309 | 2/1942 | United Kingdom | 424/38 |
| 1414121 | 11/1975 | United Kingdom | 424/157 |
| 1538280 | 1/1979 | United Kingdom | 424/156 |
| 140168 | 6/1960 | U.S.S.R. | 424/38 |

OTHER PUBLICATIONS

Richmond Choice Confections Manufacturing Methods and Formulas Manufacturing Confectioner Pub. Co. Oak Park, ILL. (1954), pp. 97–104 "Cordial Fruits".

*Primary Examiner*—Shep K. Rose
*Attorney, Agent, or Firm*—Lawrence S. Levinson; Burton Rodney

[57] ABSTRACT

A portable liquid antacid is provided which is in the form of an antacid tablet including a center portion containing an antacid in the form of a liquid, cream or gel and optionally chocolate flavorant, encased in or surrounded by a fat-containing coating, such as chocolate coating, which is resistant to air and moisture and masks the grittiness of the antacid while imparting good texture and mouth feel.

18 Claims, No Drawings

4,271,142

PORTABLE LIQUID ANTACIDS

REFERENCE TO OTHER APPLICATIONS

This application is a continuation-in-part of application Ser. No. 49,535, filed June 18, 1979, now abandoned.

BRIEF STATEMENT OF THE INVENTION

The present invention relates to an antacid tablet which is formed of a center portion containing an antacid in the form of a liquid, cream or gel, with or without flavorant, such as chocolate, enrobed in a fat-containing material, such as chocolate, and especially mint-chocolate.

BACKGROUND OF THE INVENTION

Antacids generally available are of the insoluble type which function by raising the pH of the stomach to a desired value, between 4 and 5, and maintaining this pH for some period.

Insoluble antacids depend on surface area (particle size) for their efficiency. The smaller the particle size, the larger the surface area—thus more contact between acid to be neutralized and neutralizer. It is generally accepted that liquid antacids are superior to tabletted products due to increased surface area and wettability. A liquid product offers the benefit of an insoluble antacid which is milled to a fine particle size and completely wetted to provide prompt activity in the stomach. However, liquids in the form of suspensions or emulsions, while not gritty, possess organoleptic deficiencies, causing many manufacturers to suggest co-ingestion of milk or water to alleviate symptoms of the onset of nausea.

A chewable tabletted product, moreover, requires the user to mascerate the mass with his teeth but still not attaining the small particle size and uniformity present in the liquid. Tabletted antacid products, however, offer the user convenience over the liquid—these products are more portable and contain accurate dose forms without the need for a measuring device such as a teaspoon.

Palatability and "mouth feel" are also extremely important factors in formulating antacids. Conventional metallic carbonate and hydroxide insoluble antacid materials usually have both an unpleasant mouth feel and an unpalatable taste due to chalkiness, grittiness, dryness and astringent properties of these materials. Accordingly, the practical value of these antacid materials is substantially diminished since patients finding them objectionable may fail to take them as prescribed.

In an effort to overcome the above problems, flavorings, such as peppermint oils, have been employed with antacids. Unfortunately, it has been found that the flavoring merely masks the unpleasant taste, but the chalkiness, grittiness, dryness and astringent properties still remain.

It has also been suggested to coat antacid tablets with a coating material which will not dissolve in the saliva so that it masks the disagreeable taste and mouth feel and will dissolve in the stomach. However, it has been found that most coatings suggested for such use dissolve in the intestines and not the stomach and thus provide the antacid at the wrong site. Moreover, although the coating may dissolve in the stomach, the rate of dissolution may not be fast enough to allow for sufficient neutralizing reaction time of the antacid with gastric acid before the antacid is removed from the stomach by gastric emptying.

U.S. Pat. No. 3,843,778 to Diamond et al. discloses a technique for coating antacid particles with a water insoluble, inert, non-toxic hydrocarbon oil which is formulated into suspensions or tablets which are said to be substantially free of the impalatable "mouth feel" properties associated with antacids. An electro-negative agent, such as a surfactant selected from an alkyl aryl sulfonate, or an alkyl sulfate or sulfonate, or sulfonated amides or amines; or sulfated or sulfonated esters or ethers, or a dioctyl sulfosuccinate, or a hydrated aluminum silicate, such as bentonite or kaolin, is employed to aid in adhering the oil to the electropositively charged antacid particles.

U.S. Pat. No. 3,253,988 to Scott discloses an orally administrable antacid formed of oils or fats, that is esters of higher fat acids and a trihydric alcohol, in combination with antacids. The Scott antacid may be in the form of a waxy solid, an emulsion or suspension.

DETAILED DESCRIPTION OF THE INVENTION

In accordance with the present invention, there is provided an antacid formulation which offers the advantages of portability and exact dosage form of a tablet plus fine, uniform particle size to provide the increased surface area and wettability of a liquid to achieve fast neutralization, while having a pleasing taste and a smooth and pleasant mouthfeel without hardly a trace of grittiness, chalkiness or medicinal flavor normally associated with antacids.

The antacid formulation of the invention is shaped as a tablet or pill which includes a center or core portion containing an antacid in the form of a liquid, cream or gel, and preferably an antacid masking flavorant and/or essence, which also serves as a carrier for the antacid, and a flavored fat-containing outer portion or coating surrounding or enrobing the center portion so as to prevent direct contact of the center portion with the surrounding atmosphere while masking the chalky, gritty, astringent taste of the antacid while actually enhancing the texture and mouth feel of the antacid.

It will be appreciated that the flavorants and/or essences in the core portion, where present, will together with the flavorant of the outer portion or coating, mask substantially all antacid taste normally associated with prior art antacid formulations. Thus, in a preferred embodiment of the invention, the outer portion will be chocolate and more preferably mint chocolate, which by itself will mask the antacid gritty chalky bitter taste and greatly improve texture and mouth feel of the antacid. In a most preferred embodiment, the core portion will also include a chocolate flavorant, such as chocolate, mint chocolate or other flavored chocolate, which will function with the chocolate outer portion to practically completely eliminate all antacid flavor and odor while imparting excellent texture and mouth feel to the antacid product.

The center portion or liquid, cream or gel portion of the antacid piece of the invention will generally comprise from about 25 to about 80%, and preferably from about 60 to about 70% by weight of the antacid piece, while the fat-containing outer portion or coating will comprise from about 20 to about 75%, and preferably from about 30 to about 40% by weight of the antacid piece.

The center portion will include a conventional type liquid, cream or gelled antacid formulation which will include the antacid material, and, if desired, flavorants, sweeteners, texturizers, laxatives, antiflatulents, or other additives normally found in such medicaments. As indicated, in preferred embodiments, the center portion will include a flavorant, as will be described below, which will aid in masking the taste of the antacid while imparting good taste, texture and mouthfeel. Examples of such flavorants which may be employed in the center portion to enhance the textural qualities of the antacid tablet of the invention include cocoa, chocolate, especially mint chocolate, butter, milk, cream, vanillin butter fat, egg or egg white. These flavorants may be of the natural or synthetic variety and will be present in the center portion in an amount of from 0 to about 20%, and preferably, from about 0.05% to about 0.3% by weight of the center portion formulation.

The antacid material itself will be present in the center portion in an amount within the range of from about 50 to about 95% by weight and preferably from about 60 to about 70% by weight. Examples of antacids suitable for use herein comprise any relatively water insoluble antacid acceptable to the Food & Drug Administration, such as, aluminum carbonate, aluminum hyroxide (or as aluminum hydroxide—hexitol stabilized polymer, aluminum hyroxide—magnesium hydroxide codried gel, aluminum hydroxide-magnesium trisilicate codried gel, aluminum hydroxide-sucrose powder hydrated), aluminum phosphate gel, aluminum hydroxy carbonate, dihydroxy aluminum sodium carbonate, aluminum magnesium glycinate, dihydroxy aluminum aminoacetate, aluminum phosphate, bismuth aluminate, bismuth carbonate, bismuth subcarbonate, bismuth subgallate, bismuth subnitrate, calcium carbonate, calcium phosphate, hydrated magnesium aluminate activated sulfate, magnesium aluminate, magnesium aluminosilicates, magnesium carbonate, magnesium glycinate, magnesium hydroxide, magnesium oxide and magnesium trisilicate.

Preferred antacids for use in the center portion include aluminum hydroxide gel, magnesium carbonate and mixtures thereof, aluminum phosphate gel, as well as calcium carbonate and magnesium hydroxide.

Depending on the viscosity and nature of the center portion, the center portion may contain from about 20 to about 95% water, and preferably from about 50 to about 75% water, as well as flavorant, colorant, thickener and sweetener.

In the case of a cream form of antacid, the center portion will also include from about 0.2 to about 1% by weight of thickener, such as cellulose gum and xanthan gum.

In the case of a gel form of antacid, the center portion will also include from about 0.2 to about 2% by weight of thickener, such as cellulose gum and xanthan gum.

A preferred liquid formulation for use as the center portion will contain from about 8 to about 20% by weight antacid; from about 50 to about 72% water, sweetener, flavor, colorant and the like.

Preferred gel or cream antacid formulations for use as the center portion will contain from about 8 to about 20% antacid, from about 50 to about 72% water, from about 0.2 to about 0.5% thickener, sweetener, flavor, colorant and the like.

Examples of other thickeners suitable for use in the gel and cream center portions are those which are edible and include, but are not limited to natural gums, such as carrageenan, karaya, tragacanth, methyl cellulose, veegum, sodium alginate, pectins, gelatin, and the like.

The coating or outer portion will be a fat-containing material which offers resistance to air and moisture to protect the center portion containing the antacid from spoiling, serves as a flavorant to mask the gritty chalky taste of the antacid present in the outer portion and/or center portion, and may be easily applied to and enrobed over the center portion.

The fat-containing material will be non-toxic, at least partially, and preferably totally digestable, and a solid at room temperature. Examples of fatty materials which may be employed in the outer coating include cocoa butter, butter fat, lard, milk solids, vegetable fats, coconut fat and confectioner's coatings, egg or egg white, vanillin butter fat, and cream with chocolate being preferred and mint chocolate being most preferred as the enrobing material.

The outer coating or enrobing material may also contain any one or more of the same or different antacids employed in the center portion and listed hereinbefore. Where present, the antacid will comprise from about 1 to about 20%, and preferably from about 8 to about 15% by weight of the outer coating. Antacids particularly suitable for use in the outer coating include dried aluminum hydroxide gel, bismuth subcarbonate, precipitated calcium carbonate, calcium hydroxide, dihydroxy aluminum aminoacetate, magnesium carbonate, magnesium hydroxide, magnesium oxide or magnesium trisilicate.

Suitable combinations of antacids and other additives may also be employed in both the center portion and outer coating. For example, the relative constipative effects of antacid aluminum compounds present in the center portion may be offset by the addition of a laxative causing magnesium compound present in the center portion and/or outer coating.

A surfactant approved for use in foods by the Food & Drug Administration and having an HLB value of 8 and above, may also be employed in the antacid tablets of the invention in either the center portion or outer coating in amounts ranging from about 0.05 to about 0.5% by weight.

Examples of surfactants suitable for use herein include alkyl aryl sulfonates, or alkyl sulfates, or sulfonated amides or amines, or sulfated or sulfonated esters or ethers, or alkyl sulfonates, or dioctyl sulfosuccinate and the like, or a hydrated aluminum silicate such as micronized bentonite or kaolin, or Cab-O-Sil (which is silica pigment sold under the trademark of Cab-O-Sil by Cabot Corporation of Boston, Mass.), Quso (which is a microfine silica sold under the trademark Quso by Philadelphia Quartz Co. of Philadelphia, Pa.), and the like.

The antacid particles present in the center portion and/or outer portion may be coated with a suitable oil and/or fat to further minimize the grittiness of the antacid. The fats or oils used may be of animal, vegetable or mineral origin which are substantially water-insoluble, inert, non-toxic hydrocarbon fats and oils and derivatives thereof and may comprise any of the commonly commercially available fats or oils approved by the Food and Drug Administration and having melting points constant with desired mouth feeling factors, such as melting points ranging from 80° to 110° F. The fats or oils will be employed in amounts within the range of from about 0 to about 50 and preferably from about 10 to about 35 by weight of the center portion and/or outer portion. Examples of fats or oils suitable for use herein include hydrogenated tallow, hydrogenated vegetable oil, almond oil, coconut oil, corn oil, cottonseed oil, refined linseed oil, light liquid petrolatum, heavy liquid petrolatum, olein, olive oil, palm oil, peanut oil, persic oil, sesame oil, soybean oil or safflower oil.

Preferred oils include hydrogenated tallow, hydrogenated vegetable oil, corn oil, light and heavy liquid petrolatum, olein, olive oil, peanut oil and soybean oil.

Surprisingly, it has been found that where the edible fat and/or oil is employed in conjunction with the flavorant for the center portion and/or outer portion, the flavorant actually enhances the effect of the edible fats and oils to minimize the grittiness of the antacids.

The antacid tablet of the invention may also include other pharmaceutically acceptable agents present in the center portion and/or outer coating such as sweetening agents, including sugars, sugar alcohols, and synthetic sweeteners such as sorbitol, xylitol, saccharin salts, free acid form of saccharin, cyclamate salts, free cyclamic acid, dihydrochalcones, L-aspartyl-L-phenylalanine methyl ester, as well as coloring agents, flavoring agents, disintegrating agents (in the outer coating) such as starch, binding agents, lubricants such as calcium stearate, stearic acid, magnesium stearate and the like.

The antacid piece or tablet of the invention may be manufactured employing conventional techniques used in making liquid, cream or gel filled confections, such as chocolate covered cherries or toffees or other candies.

In one method of manufacture, a suspension of antacid materials including antacid, water, and sweetener is formed; sodium alginate is added to the antacid suspension and a portion of the mixture is dropped into a calcium chloride bath. The alginate cross-links with the calcium into an irreversible layer of calcium alginate which temporarily surrounds the entire volume of antacid suspension. This "contained" suspension can then be placed into a suitable chocolate container and covered or can be dropped through a chocolate enrober or bath.

Alternatively, commercially available chocolate handling equipment having enrobing or center filling capabilities may be employed to form antacid pieces or tablets of the invention.

The following represents preferred antacid tablet formulations in accordance with the present invention.

| Preferred Antacid Tablet Formulations | |
|---|---|
| | Ranges of Amounts % by Weight |
| Center Portion | |
| Liquid Formulation | |
| Antacid (magnesium hydroxide and/or aluminum hydroxide) | 8-20 |
| Water | 50-72 |
| Sweetener | 20-30 |
| Flavorant | 0.2-1 |
| Fat or oil | 0.2-20 |
| Cream Formulation | |
| Antacid (magnesium hydroxide and/or aluminum hydroxide) | 8-20 |
| Water | 50-72 |
| Sweetener | 20-30 |
| Flavorant | 0.2-1 |
| Thickener | 0.2-1 |
| Fat or oil | 0.2-20 |
| Gel Formulation | |
| Antacid (magnesium hydroxide and/or aluminum hydroxide) | 8-20 |
| Water | 50-72 |

| Preferred Antacid Tablet Formulations -continued | |
|---|---|
| | Ranges of Amounts % by Weight |
| Sweetener | 20-30 |
| Flavorant | 0.2-1 |
| Thickener | 0.2-2 |
| Fat or oil | 0.2-20 |
| Outer Coating | |
| Chocolate (preferably mint chocolate) | 84-92 |
| Antacid (dried aluminum hydroxide gel or magnesium hydroxide) | 0-15 |
| Colorant | 0.015-0.02 |
| Other flavorant | 0.2-1 |

The Examples represent preferred embodiments of the present invention.

EXAMPLE 1

An antacid suspension containing 13.3 parts aluminum hydroxide/magnesium hydroxide (50:50), 50 parts water, 0.5 part chocolate flavor, and 36.2 parts sugar sweetener is prepared by thoroughly and intensively mixing the above ingredients in a standard V-type blender.

Sodium alginate is mixed into the antacid suspension to attain a 2% alginate concentration. Aliquots of 3 ml to 5 ml of this mixture are dropped through a glass column of 2% calcium chloride solution.

Antacid pieces or droplets are formed having a cross-linked moisture resistant surface. The antacid pieces are deposited in pre-formed mint chocolate shells and then covered with molten mint chocolate and allowed to harden.

The final antacid pieces contain about 33% by weight outer coating in the form of mint chocolate, and 67% by weight center portion of which 9% by weight (based on the weight of the entire piece) is antacid, 33.5% is water and 24.6% is sweetener.

The antacid piece so made is found to have a pleasant taste and smooth mouth feel, good stability and is an excellent antacid. The mint chocolate in the outer coating and the chocolate in the center portion are found to effectively mask the gritty taste of the antacid while greatly contributing to the texture and mouth feel of the product.

EXAMPLE 2

An antacid suspension containing 13.3 parts calcium carbonate, 50 parts water and 36.7 parts dextrose sweetener is prepared by thoroughly blending the above ingredients.

The antacid suspension is poured into preformed mint chocolate shells and then covered with molten mint chocolate and allowed to harden.

The final antacid pieces contain about 67% by weight center portion of which 9% by weight (based on the weight of the piece) is antacid.

The above antacid piece is found to have properties similar to that described with respect to the antacid of Example 1.

EXAMPLE 3

An antacid piece or tablet is prepared according to the procedure described in Example 1 except that solid antacid, namely dried aluminum hydroxide gel is blended into the mint chocolate phase outer portion before the center portion is added thereto.

The antacid tablet produced has the following composition.

| Ingredient | Parts by Weight |
| --- | --- |
| Center Portion | |
| Antacid (aluminum hydroxide/ magnesium hydroxide 50:50) | 25 |
| Excipients (water, sweetener, flavor) | 65 |
| Chocolate | 10 |
| (Outer Portion) | |
| Mint Chocolate | 86.8 |
| Antacid (dried aluminum hydroxide gel) | 13.2 |

The above antacid is found to have similar properties as the antacid pieces of Examples 1 and 2.

EXAMPLE 4

An antacid piece or tablet is prepared according to the procedure of Example 1 except that 2% simethicone is added to the ingredients employed in forming the antacid suspension.

EXAMPLE 5

An antacid piece or tablet is formed as described in Example 1 except that the cross-linked "droplets" of antacid suspension are dipped into a vat of chocolate coating and then are allowed to harden to form the finished piece.

EXAMPLE 6

An antacid piece or tablet is formed as described in Example 1 except that the cross-linked "droplets" of antacid suspension are spray coated with chocolate and dried in a fluidized bed-type operation.

EXAMPLE 7

An antacid tablet is formed as described in Example 1 except that the antacid suspension is deposited into molds containing hardened chocolate as in a typical shell molding operation. The deposited antacid suspension is coated with molten chocolate to completely enclose the antacid suspension.

EXAMPLE 8

Antacid particles for use in preparing an antacid composition in accordance with the invention is prepared as outlined below.

| Antacid Particles | Parts by Weight |
| --- | --- |
| Magnesium carbonate - aluminum hydroxide (1:1) co-dried gel | 20 |
| Calcium stearate | 1 |
| Hydrogenated tallow (Sterotex) | 1 |
| Hydrogenated vegetable oil | 1 |
| Polyoxyethylene sorbitan fatty acid ester (Tween 60) | 0.2 |

The antacid (magnesium carbonate-aluminum hydroxide) calcium stearate, hydrogenated tallow, hydrogenated vegetable oil and polyoxyethylene sorbitan fatty acid ester are intensively mixed in a Gifford-Wood Homogenizer until an average particle size of about 50 milimicrons is achieved and substantially complete homogeneity of the materials accomplished.

A portion of the above antacid particles (18.42 parts) are then suspended in 30.18 parts water, 28.28 parts chocolate and 23.12 parts sugar by thoroughly and intensively mixing these ingredients in a standard V-type blender.

Sodium alginate is mixed into the antacid suspension to attain a 2% alginate concentration. Aliquots of 3 ml to 5 ml of this mixture are dropped through a glass column of 2% calcium chloride solution.

Antacid pieces or droplets are formed having a cross-linked moisture resistant surface. The antacid pieces are deposited in pre-formed mint chocolate shells and then covered with molten mint chocolate containing 30% by weight of fat. The molten chocolate is allowed to harden.

The final antacid pieces contain about 33% by weight outer coating in the form of mint chocolate, and 67% by weight center portion of which 12.34% by weight (based on the weight of the entire piece) is antacid, 20.22% is water, 48.49% is sweetener and 18.95% is fat.

The antacid piece so made is found to have a pleasant taste and smooth mouth feel, good stability and is an excellent antacid. The mint chocolate in the outer coating in combination with the fat and oil coatings are found to effectively mask the gritty taste of the antacid while greatly contributing to the texture and mouth feel of the product.

What is claimed is:

1. An antacid piece consisting essentially of a center portion and an outer portion surrounding said center portion, said center portion consisting essentially of an antacid in the form of a liquid, cream or gel, and optionally a flavorant to mask the grittiness of the antacid and enhance the textural qualities of the antacid piece, and said outer portion consisting essentially of a fat containing material comprising a chocolate which is resistant to air and moisture for protecting said center portion and masking the grittiness of the antacid.

2. The antacid piece as defined in claim 1 wherein the center portion includes said flavorant which is a natural or synthetic material including cocoa, chocolate, butter, milk, cream, vanillin butter fat, egg or egg white.

3. The antacid piece as defined in claim 2 wherein said flavorant comprises from about 0.2 to about 20% by weight of said center portion.

4. The antacid piece as defined in claim 2 wherein the antacid in the center portion comprises antacid particles and a carrier therefor, said antacid particles being coated with an oil and/or fat which in conjunction with the flavorant masks the grittiness of the antacid while imparting good texture and mouth feel.

5. The antacid piece as defined in claim 1 wherein the center portion comprises from about 25 to about 80% by weight of said antacid piece, and said outer coating comprises from about 20 about about 75% by weight of said antacid piece.

6. The antacid piece as defined in claim 1 wherein said antacid present in said center portion comprises from about 8 to about 20% by weight of said antacid piece.

7. The antacid piece as defined in claim 1 wherein said outer portion consists essentially of a mint chocolate shell or coating.

8. The antacid piece as defined in claim 1 wherein said outer portion includes antacid particles dispersed therein.

9. The antacid piece as defined in claim 8 wherein said antacid particles are coated with an oil and/or fat, which in conjunction with said chocolate masks the grittiness of the antacid while imparting good texture and mouth feel.

10. The antacid piece as defined in claim 1 wherein said center portion consists essentially of a liquid comprising from about 8 to about 20% antacid, from about 50 to about 72% water, all percentages being based on the weight of the center portion, and sweetener and optionally flavorant.

11. The antacid piece as defined in claim 1 wherein said center portion consists essentially of a cream comprising from about 8 to about 20% antacid, from about 50 to about 72% water, from about 0.2 to about 1% by weight thickener, and from about 0 to about 20% by weight chocolate flavorant, all of said percentages being based on the weight of the center portion, and optionally sweetener and flavor.

12. The antacid as defined in claim 1 wherein said center portion consists essentially of a gel comprising from about 8 to about 20% by weight antacid, from about 50 to about 72% by weight water, from about 0.2 to about 2% by weight thickener, and from 0 to about 20% by weight chocolate flavorant, all of said percentages being based upon the weight of said center portion, and optionally sweetener and flavor.

13. The antacid piece as defined in claim 1 wherein said antacid present in said center portion is aluminum hydroxide gel, aluminum phosphate gel, bismuth magma, chalk mixture, magnesium carbonate, magnesium magma or magnesium trisilicate.

14. The antacid piece as defined in claim 1 wherein said outer portion includes an antacid comprising dried aluminum hydroxide gel, bismuth subcarbonate, precipitated calcium carbonate, calcium hydroxide, dihydroxy aluminum aminoacetate, magnesium carbonate, magnesium hydroxide, magnesium oxide or magnesium trisilicate.

15. The antacid piece as defined in claim 14 wherein said antacid comprises from about 8 to about 15% by weight of said outer portion.

16. The antacid piece as defined in claim 1 wherein said antacid material present in said center portion is aluminum hydroxide, magnesium hydroxide combinations thereof or calcium carbonate and said outer portion comprises chocolate.

17. The antacid piece as defined in claim 16 wherein said center portion further includes cellulose gum or xanthan gum thickener.

18. The antacid piece as defined in claim 16 wherein said outer portion further includes calcium carbonate antacid.

* * * * *